United States Patent
Pancook

(10) Patent No.: US 12,195,548 B2
(45) Date of Patent: *Jan. 14, 2025

(54) CHIMERIC CANINE ANTI-CD20 ANTIBODY

(71) Applicant: Elanco US Inc., Greenfield, IN (US)

(72) Inventor: James David Pancook, San Diego, CA (US)

(73) Assignee: Elanco US Inc., Greenfield, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,769

(22) Filed: Apr. 20, 2023

(65) Prior Publication Data

US 2023/0257476 A1    Aug. 17, 2023

Related U.S. Application Data

(63) Continuation of application No. 17/167,685, filed on Feb. 4, 2021, now abandoned, which is a continuation of application No. 16/683,518, filed on Nov. 14, 2019, now Pat. No. 10,941,206, which is a continuation of application No. 16/073,927, filed as application No. PCT/US2017/017337 on Feb. 10, 2017, now Pat. No. 10,519,244.

(60) Provisional application No. 62/296,729, filed on Feb. 18, 2016.

(51) Int. Cl.
| | |
|---|---|
| C07K 16/28 | (2006.01) |
| A61K 39/00 | (2006.01) |
| A61K 39/395 | (2006.01) |
| C07K 16/12 | (2006.01) |
| G01N 33/53 | (2006.01) |

(52) U.S. Cl.
CPC .......... *C07K 16/2887* (2013.01); *A61K 39/00* (2013.01); *A61K 39/395* (2013.01); *C07K 16/1271* (2013.01); *C07K 16/2809* (2013.01); *G01N 33/53* (2013.01); *A61K 2039/505* (2013.01); *C07K 2317/24* (2013.01); *C07K 2317/31* (2013.01); *C07K 2317/33* (2013.01)

(58) Field of Classification Search
None
See application file for complete search history.

(56) References Cited

U.S. PATENT DOCUMENTS

| | | |
|---|---|---|
| 10,519,244 B2 | 12/2019 | Pancook |
| 10,941,206 B2 | 3/2021 | Pancook |
| 2009/0169550 A1 | 7/2009 | Dummer |

FOREIGN PATENT DOCUMENTS

| | | |
|---|---|---|
| CN | 1662557 A | 8/2005 |
| CN | 1874788 A | 12/2006 |
| JP | 2007516231 A | 6/2007 |
| JP | 2013520990 A | 6/2013 |
| WO | 2004103404 A1 | 12/2004 |
| WO | 2010110838 A2 | 9/2010 |
| WO | 2011109108 A1 | 9/2011 |
| WO | 2013054127 A1 | 4/2013 |
| WO | 2013063186 A2 | 5/2013 |
| WO | 2016016859 A1 | 4/2016 |

OTHER PUBLICATIONS

Chiu et al., "Antibody Structure and Function: The Basis for Engineering Therapeutics," Antibodies (Basel); 8(4):55 (Dec. 3, 2019).
Chothia et al., "Canonical Structures for the Hypervariable Regions of Immunoglobulins," Journal of Molecular Biology 196, No. 4: 901-917 (1987).
Ettinger et al., "Principles of Treatment for Canine Lymphoma," Clinical Techniques in Small Animal Practice, vol. 18, No. 2: pp. 92-97 (May 2003).
Kabat, et al., "Attempts to locate complementarity-determining residues in the variable positions of light and heavy chains," Annals of the New York Academy of Sciences 190, No. 1: 382-393 (1971).
Kabat et al., Sequences of Proteins of Immunological Interest, Fifth Edition, U.S. Department of Health and Human Services, NIH Publication No. 91-3242 (1991).
Kabat et al., "Unusual distributions of amino acids in complementarity determining (hypervariable) segments of heavy and light chains of immunoglobulins and their possible roles in specificity of antibody-combining sites," Journal of Biological Chemistry 252, No. 19: 6609-6616 (1977).
Kunik et al., "Structural Consensus among Antibodies Defines the Antigen Binding Site," PLoS Comput Biol.; 8(2): e1002388 (Feb. 2012).
MacCallum et al., "Antibody-antigen interactions: contact analysis and binding site topography," Journal of molecular biology 262, No. 5: 732-745 (1996).
North et al., "A new clustering of antibody CDR loop conformations," Journal of molecular biology 406, No. 2: 228-256 (2011).
Patent Cooperation Treaty International Search Report and the Written Opinion of the International Searching Authority pertaining to International Application No. PCT/2017/017337; Date of Mailing: Apr. 19, 2017.

*Primary Examiner* — Nora M Rooney
(74) *Attorney, Agent, or Firm* — McBee, Moore & Vanik IP, LLC

(57) ABSTRACT

The disclosure relates to caninized chimeric anti-CD20 antibodies to the canine protein CD20 and methods of use to treat certain disorders such as non-Hoiodgkins B-cell lymphoma in dogs.

7 Claims, 1 Drawing Sheet
Specification includes a Sequence Listing.

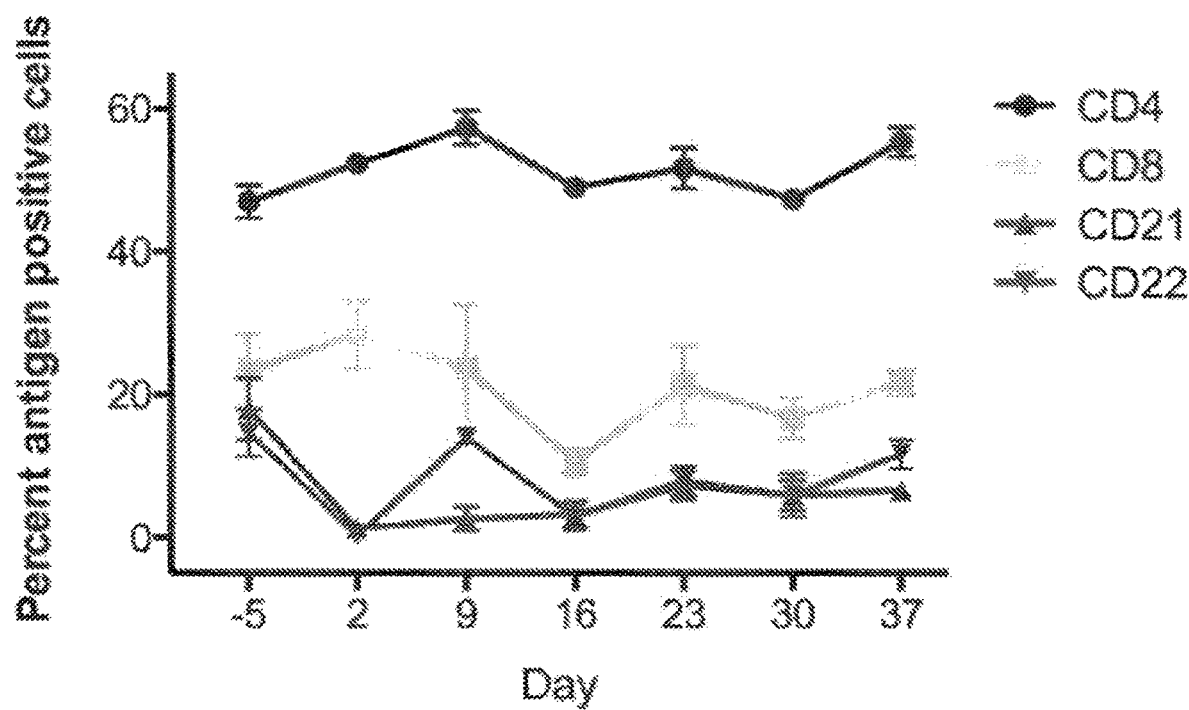

CHIMERIC CANINE ANTI-CD20 ANTIBODY

CROSS-REFERENCE TO RELATED APPLICATIONS

This application is a continuation application of U.S. application Ser. No. 17/167,685, filed 4 Feb. 2021, which is a continuation application of U.S. application Ser. No. 16/683,518, filed 14 Nov. 2019 (now U.S. patent Ser. No. 10/941,206, issued 9 Mar. 2021), which is a continuation application of U.S. application Ser. No. 16/073,927, filed 30 Jul. 2018 (now U.S. patent Ser. No. 10/519,244, issued 31 Dec. 2019), which is the National Stage entry of International Application No. PCT/US2017/017337, filed 10 Feb. 2017, which claims priority to U.S. Provisional Application No. 62/296,729, filed 18 Feb. 2016, the entire contents of each of which are incorporated herein by reference.

REFERENCE TO SEQUENCE LISTING SUBMITTED AS A COMPLIANT ASCII TEXT FILE (.xml)

A Sequence Listing is submitted herewith as an ASCII compliant text file named "2920951-474004_Sequence_Listing_ST26" created on 20 Apr. 2023 and having a size of 27,871 bytes as permitted under 37 C.F.R. § 1.821 (c). The material in the aforementioned file is hereby incorporated by reference in its entirety.

BACKGROUND OF THE INVENTION

Field

The present invention relates to caninized chimeric anti-CD20 antibodies to the canine protein CD20 and methods of use to treat certain disorders such as non-Hodgkins B3-cell lymphoma in dogs.

The present invention is in the field of treatment of cancer.

SUMMARY

Canine lymphomas are a diverse group of cancers, and are among the most common cancers diagnosed in dogs. They collectively represent approximately 7-14% of all cancers diagnosed in dogs. There are over 30 described types of canine lymphoma, and these cancers vary tremendously in their behavior. Some progress rapidly and are acutely life-threatening without treatment, while others progress very slowly and are managed as chronic, indolent diseases. Lymphomas may affect any organ in the body, but most commonly originate in lymph nodes, before spreading to other organs such as the spleen, liver, and bone marrow.

CD20 is a cell-surface protein with four transmembrane spanning regions. The CD20 molecule is involved in regulation of B-cell proliferation and differentiation. The CD20 antigen is present exclusively on the surface of almost all B-ceils, both normal and malignant.

Rituximab is a chimeric monoclonal antibody against the human protein CD20 which is primarily found on the surface of immune system B-cells. Rituximab destroys B-cells and is therefore used to treat diseases in humans which are characterized by excessive numbers of B-ceils, overactive B-cells, or dysfunctional B-cells. This includes many lymphomas, leukemias, transplant rejection, and autoimmune disorders.

Rituximab destroys both normal and malignant human B-cells that have CD20 on their surfaces. The effect results in the elimination of B-cells (including the cancerous ones) from the body, allowing a new population of healthy B-cells to devel op from lymphoid stem cells.

Unfortunately, a cure for canine lymphomas still remains elusive and there exists a need for more and different therapies that may prove to be effective in treating them.

K9LO-133 is a chimeric anti-CD20 antibody that targets mature B-lymphocytes in dogs. K9LO-133 binds to CD20 on canine B-lymphocytes. K9LO-1.33 is potentially useful for treatment for non-Hodgkins B cell lymphoma and other types of lymphoma in dogs.

Accordingly, the present invention provides an antibody that specifically binds to canine CD20. The present invention also provides a method of treating lymphoma in a canine patient by administering to a lymphoma cancer canine patient in need of such treatment an effective amount of an antibody that specifically binds to canine CD20. The present invention provides for a pharmaceutical composition including an antibody that specifically binds to canine CD20, and one or more pharmaceutically acceptable carriers, diluents, or excipients. The present invention also provides an antibody that specifically binds to canine CD20 and also binds to protein A.

BRIEF DESCRIPTION OF THE DRAWINGS

FIG. 1 depicts the serum levels of B-lymphocytes CD21+ and CD22+ and T-lymphocytes CD4+ and CD8+ from −5 to 37 days in dogs treated with K9LO-133 antibody.

DETAILED DESCRIPTION

Unless indicated otherwise, the term "antibody" (Ab) refers to an immunoglobulin molecule comprising two heavy chains (HC) and two light chains (LC) interconnected by disulfide bonds. The amino terminal portion of each chain includes a variable region of about 100 to about 110 amino acids primarily responsible for antigen recognition via the complementarity determining regions (CDRs) contained therein. The carboxy-terminal portion of each chain defines a constant region primarily responsible for effector function.

As used herein, the term "antigen-binding fragment" refers to any antibody fragment that retains the ability to bind to its antigen. Such "antigen-binding fragments" can be selected from the group consisting of Fv, scFv, Fab, F(ab')$_2$, Fab', scFv-Fc fragments and diabodies. An antigen-binding fragment of an antibody will typically comprise at least one variable region. Preferably, an antigen-binding fragment comprises a heavy chain variable region (HCVR) and a light chain variable region (LCVR). More preferably, an antigen-binding fragment as used herein comprises a HCVR and a LCVR which confers antigen-binding specificity to canine CD20 (i.e., a "canine CD20 binding fragment").

As used herein, the terms "complementarity determining region" and "CDR", refer to the non-contiguous antigen combining sites found within the variable region of LC and HC polypeptides of an antibody or an antigen-binding fragment thereof. These particular regions have been described by others including Kabat, et al., Ann. NY Acad. Sci. 190:382-93 (1971), Kabat et al., J, Biol. Chem. 252: 6609-6616 (1977), Kabat, et al, Sequences of Proteins of Immunological Interest, Fifth Edition, U.S. Department of Health and Human Services, NIH Publication No. 91-3242 (1991); Chothia, et al, J. Mol. Biol. 196:901-917 (1987); MacCallum, et al., . J. Mol. Biol., 262:732-745 (1996); and North, et al., J. Mol. Biol. 406, 228-256 (2011), where the definitions include overlapping or subsets of amino acid residues when compared against each other.

As used herein, the term "light chain variable region" refers to a portion of a LC of an antibody molecule that includes amino acid sequences of Complementarity Determining Regions (CDRs; i.e., LCDR1, LCDR2, and LCDR3), and Light Framework Regions (LFRWs).

As used herein, the term "heavy chain variable region (HCVR)" refers to a portion of a HC of an antibody molecule that includes amino acid sequences of Complementarity Determining Regions (CDRs; i.e., HCDR1, HCDR2, and HCDR3), and Heavy Framework Regions (HFRWs).

The CDRs are interspersed with regions that are more conserved, termed framework regions ("FRW"). Each LCVR and HCVR, is composed of three CDRs and four FRWs, arranged from amino-terminus to carboxy-terminus in the following order: FRWI, CDRI, FRW2, CDR2, FRW3, CDR3, FRW4. The three CDRs of the light chain are referred to as "LCDR1, LCDR2, and LCDR3" and the three CDRs of the HC are referred to as "HCDR1, HCDR2, and HCDR3." The CDRs contain most of the residues which form specific interactions with the antigen. The numbering and positioning of CDR amino acid residues within the LCVR and HCVR regions is in accordance with known conventions (e.g., Kabat (1991). Chothia (1987), and/or North (2011)). In different embodiments of the invention, the FRWs of the antibody may be identical to the germline sequences, or may be naturally or artificially modified.

In certain embodiments, the anti-CD20 Ab for the methods and/or uses of the present invention is altered to increase or decrease the extent to which the antibody is glycosylated. Addition or deletion of glycosylation sites to an antibody may be conveniently accomplished by altering the amino acid sequence such that one or more glycosylation sites is created or removed.

Unless indicated otherwise, when referring to an amino acid residue in an antibody by a number, the EU numbering system is used herein as it is conventionally used in the art (see, Kabat, et al., Sequences of Proteins of Immunological Interest, Fifth Edition, U.S.

Department of Health and Human Services, NTH Publication No. 91-3242 (1991), for example).

As used herein, the term "kit" refers to a package comprising at least two separate containers, wherein a first container contains a K9LO-133 Ab and a second container contains pharmaceutically acceptable carriers, diluents, or excipients. As used herein, the term "kit" also refers to a package comprising at least two separate containers, wherein a first container contains K9LO-133 Ab, and another antibody preferably for the treatment of cancers other than lymphomas. A "kit" may also include instructions to administer all or a portion of the contents of these first and second containers to a cancer patient. Optionally, these kits also include a third container containing a composition comprising a known chemotherapeutic agent.

As used herein, the terms "treating," "to treat," or "treatment" refers to restraining, slowing, stopping, reducing, or reversing the progression or severity of an existing symptom, disorder, condition, or disease.

As used herein, the term "effective amount" refers to the amount or dose of a caninized anti-CD20 Ab which, upon single or multiple dose administration to the patient, provides an effective response in the patient under diagnosis or treatment.

As used herein, the terms "effective response" of a patient or a patient's "responsiveness" to treatment with a combination of agents, or "therapeutic effect" refers to the clinical or therapeutic benefit(s) imparted to a patient upon administration of a caninized anti-CD20 Ab. Such benefit(s) include any one or more of: extending survival (including overall survival and progression free survival); resulting in an objective response (including a complete response or a partial response); decreasing amount of B-cells, decreasing concentration of B-cells in a patient's blood or other tissues and fluids, tumor regression, tumor weight or size shrinkage, longer time to disease progression, increased duration of survival, longer progression free sumval, improved overall response rate, increased duration of response, and improved quality of life and/or improving signs or symptoms of cancer, etc.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species or breed of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication, and other relevant circumstances.

K9LO-133

AME-133V is a second generation humanized IgG1 monoclonal antibody. K9LO-133 is a partially caninized (human variable regions with canine constant regions) isotype C monoclonal antibody version of AME-133 V that specifically binds to CD20 protein in dogs.

In an embodiment, K9LO-133 contains engineered variable regions of the heavy and light chains, CDRs and frameworks. In an embodiment, a residue variant in LCDR1 of K9LO-133 is introduced. In an embodiment, the residue variant in LCDR1 of K9LO-133 is V165G. In an embodiment, a variant hinge region is introduced. In an embodiment, a variant region downstream of the hinge is added. In an embodiment, the variant region downstream of the hinge allows K9LO-133 to bind to protein A.

K9LO-133 has a heavy chain amino acid sequence corresponding to SEQ ID NO: 1 and a corresponding nucleotide sequence SEQ ID NO: 2 that encodes for the amino acid of SEQ ID NO: 1. K9LO-133 has a heavy chain variable region sequence of SEQ ID NO: 3. The heavy chain variable sequence region further consists of HFWK 1 (SEQ ID NO: 4), HCDR1 (SEQ ID NO: 5), HFWK 2 (SEQ ID NO: 6), HCDR2 (SEQ ID NO: 7), HFWK3 (SEQ ID NO: 8), and FICDR3 (SEQ ID NO: 9).

K9LO-133 has a light chain amino acid sequence corresponding to SEQ ID NO: 10 and a corresponding nucleotide sequence SEQ ID NO: 11 that encodes for the amino acid of SEQ ID NO: 10. K9LO-133 has a light chain variable region sequence of SEQ ID NO: 12. The light chain variable sequence region further consists of LFWK 1 (SEQ ID NO: 13), LCDR1 (SEQ ID NO: 14), LFWK 2 (SEQ ID NO: 15), LCDR2 (SEQ ID NO: 16), LFWK 3 (SEQ ID NO: 17), LCDR3 (SEQ ID NO: 18), and a J region (SEQ ID NO: 19).

CD20 Expression in Canine Lymphoma Tissue CD20 expression in canine lymphoma tissue can be evaluated using immunohistochemistry (IHC) with AME-133 V and K9LO-133. In order to detect binding, AME-133V and K9LO-133 can be applied to cryosections of canine lymphoma samples at one concentration, for example 10 µg/mL.

In addition, AME-133V and K9LO-133 can be substituted with an appropriate species and isotype matched negative control antibody which has a different antigenic specificity from that of detection antibodies, for example, either human IgG1, designated HuIgG1, (for AME-133V) and dog IgG, designated DgIgG (for K9LO-133). Other controls can be produced by omission of the detection antibodies or negative control antibodies from the assay (assay control).

When tested essentially as described above, AME-133V and K9LO-133 produced 3+ staining of >75% of the positive control mononuclear leucocytes. For K9LO-133, 3+ staining was observed in lymphocytes in the white pulp in canine spleen, AME-133V and K9LO-133 did not specifically react with the negative control smooth myocytes (specifically nuclei for K9LO-133) in canine spleen. The negative control antibodies, HuIgGI and DgIgG, did not specifically react with either the positive or negative control tissue elements in canine spleen, There also was no staining of the assay control slides. The specific reactions of AME-133V and K9LO-133 with the positive control tissue element and the lack of specific reactivity with the negative control tissue element, as well as the lack of reactivity of the negative control antibody, indicated that the assay was sensitive, specific, and reproducible.

CD20 was detected in >75% of the neoplastic cells in 8 of 10 canine lymphoma samples examined. In the other samples, 1-5% of neoplastic cells were positively stained for CD20.

K9LO-133 Treated Dogs

The human dose for Rituximab for the treatment of non-Hodgkin's lymphoma is 375 mg/nr. Generally, a canine chem© therapeutic dose is 40% of a human dose, irrespective of cancer type. Therefore, and without being bound by theory, an appropriate starting dose of an anti-CD20 antibody for canine non-Hodgkin's lymphoma is about 150 mg/m$^2$. In order to adjust for body surface area of a 7 kg dog, the 150 mg/m$^2$ number was corrected by multiplying by 0.37. The resulting dose of K9LO-133 administered to the dogs was about 57 mg/dog.

In an embodiment, the dose of K9LO-133 administered to a dog is from about 140 mg to about 160 mg per meter squared of body surface area. In an embodiment, the dose of K9LO-133 administered to a dog is from about 130 mg to about 170 mg per meter squared of body surface area. In an embodiment, the dose of K9LO-133 administered to a dog is from about 110 mg to about 190 mg per meter squared of body surface area. In an embodiment, the dose of K9L0-133 administered to a dog is from about 50 mg to about 250 mg per meter squared of body surface area.

In an embodiment the dose of K9LO-133 administered to a dog is from about 50 mg/dog to about 60 mg/dog. In another embodiment, the dose of K9LO-133 administered to a dog is from about 40 mg/dog to about 70 mg/dog. In an embodiment, the dose of K9LO-133 administered to a dog is from about 30 mg/dog to about 100 mg/dog. In an embodiment, the dose of 1K9L0-133 administered to a dog is from about 10 mg/dog to about 1000 mg/dog.

The efficacy of K9LO-133 was determined in dogs by dosing them intravenously (IV) at about 150 mg/m$^2$ on Days 0, 7, and 35. Three female Beagle dogs were acclimated to study conditions for seven days during which they were subjected to physical examinations; body weight measurements; and daily clinical observations. On dosing days, dogs were dosed with 57 mg of K9LO-133 via slow IV infusion at a rate of 0.5 to I mL/min.

Blood was collected for determination of lymphocyte proportions and serum retention on Days −5, 2, 9, 16, 23, 30, and 37.

As depicted in FIG. 1, there was a drop in the proportion of blood B-lymphocytes after treatment with K9LO-133. The proportion of B-lymphocytes (CD21+ and CD22+) dropped on Day 2, showed a recovery between Days 2 and 30, but had not yet returned to baseline levels by Day 37. CD8+ T-lymphocytes showed a decrease on Day 16 but had returned to baseline levels by Day 23. The proportion of CD4+ T-lymphocytes remained relatively constant.

Thus, IV administration of K9LO-133 reduced B-lymphocyte counts in circulation with a transient decrease in CD 8+ T-lymphocytes in treated dogs.

In an aspect, disclosed herein is an antibody having a light chain variable region (LCVR) whose amino acid sequence is that given in SEQ ID NO: 12, and a heavy chain variable region (HCVR) whose amino acid sequence is that given in SEQ ID NO: 3. In an embodiment, the antibody specifically binds to canine CD20.

In another aspect, disclosed herein is an antibody having a light chain (LC) whose amino acid sequence is that given in SEQ ID NO: 10, and a heavy chain (HC) whose amino acid sequence is that given in SEQ ID NO: 1 is disclosed. In an embodiment, the antibody specifically binds to canine CD20, In an aspect, disclosed herein is an antibody having two light chains (LC) each having an amino acid sequence that is given in SEQ ID NO: 10, and two heavy chains (HC) each having an amino acid sequence that is given in SEQ ID NO: 1. In an embodiment, the antibody specifically binds to canine CD20.

In another aspect, a method of treating lymphoma in a canine patient is disclosed that includes administering to a lymphoma cancer canine patient in need of such treatment an effective amount of an antibody having a light chain variable region (LCVR) whose amino acid sequence is that given in SEQ ID NO: 12, and a heavy chain variable region (HCVR) whose amino acid sequence is that given in SEQ ID NO: 3, and the antibody specifically binds to canine CD20. In an embodiment, the antibody has a light chain (LC) whose amino acid sequence is that given in SEQ ID NO: 10, and a heavy chain (HC) whose amino acid sequence is that given in SEQ ID NO: 1. In an embodiment, the antibody is K9LO-133.

In an aspect, a kit is disclosed that has a pharmaceutical composition containing K9LO-133 with one or more pharmaceutically acceptable carriers, diluents, or excipients.

In another aspect, an antibody is disclosed having a light chain (LC) whose amino acid sequence is that given in SEQ ID NO: 10, and a heavy chain (HC) whose amino acid sequence is that given in SEQ ID NO: 1, and the antibody specifically binds to canine CD20, and the antibody binds to protein A.

EXAMPLES

K9LO-133

K9LO-133 can be supplied in 10 niM citrate, 150 mN NaCl, pH-6.5 at 26.3 mg/mL. The vehicle can be physiological saline at 0.9% NaCl.

Dosing of K9LO-133 can be based on body surface area, which was estimated for the dogs in this study to be 0.37 m$^2$. Each dog received 150 mg/m$^2$ (57 mg) of K9LO-133 at each dose. Doses were prepared by drawing up 57 mg (2.2 mL) of K9LO-133 and diluting in 27.8 mL of physiologic saline to bring the total volume to 30 mL for infusion.

Flow Cytometry

T-lymphocyte (CD4+ and CD8+) and B-lymphocyte (CD21+ and CD22+) amounts can be determined by flow cytometry. Blood collection for flow cytometry was performed prior to feeding. Approximately 1 mL of EDTA anti-coagulated blood was provided from 3 dogs at baseline (day −5), and on Days 2, 9, 16, 23, 30 and 37. Red blood cells were lysed with ammonium chloride hypotonic buffer, and leukocytes were stained with antibodies reactive with canine CD4, CD8, CD21 and CD22. Then, unbound antibodies were removed and the acquisition of 10,000 leukocyte events in a FACScan or a FACS Aria flow cytometer were obtained.

Lymphoma Samples Ten frozen canine lymphoma samples were trimmed and embedded in Tissue-Tek® OCT (Optimal Cutting Temperature) compound and stored in a freezer set to maintain −80° C. until sectioning. Sections were cut at approximately 5μm to generate an appropriate number of slides for subsequent IHC staining.

Immunohistochemistry Staining

Sections from each lymphoma sample were stained using AME-133V, a human IgG1 monoclonal antibody directed against human CD20, and K9LO-133, a chimeric canine isotype C monoclonal antibody directed against canine CD20, using IHC as detailed below. AME-133V was in a 19.5 mg/mL solution in phosphate-buffered saline (PBS), pH 7.4. K9LO-133 was in a 2.5 mg/mL solution in PBS, pH 7.4. IHC staining was performed including use of positive and negative control materials in each staining run and using additional slides for the negative control antibody and assay control to ensure stain specificity. The staining procedures, primary and secondary antibody dilutions, and controls for AME-133V were qualified in preliminary staining runs. The staining procedures, primary and secondary antibody dilutions, and controls for K9LO-133 were qualified in a methods development staining run.

AME-133V Staining

The indirect immunoperoxidase procedure can be used to stain the canine lymphoma tissue with AME-133V to detect CD20. Slides were fixed in acetone for 10 minutes at room temperature at the time of sectioning. Acetone-fixed cryosections were rinsed twice in phosphate-buffered saline, 0.15 M NaCl, pH 7.2 PBS. Endogenous peroxidase was then quenched by incubation of the slides with Biocare PeroxAbolish for 5 minutes at room temperature. Next, the slides were rinsed twice with PBS, incubated with the avidin solution for 15 minutes, rinsed once with PBS, incubated with the biotin solution for 15 minutes, and rinsed once with PBS. The slides were then treated with a protein block designed to reduce nonspecific binding for 20 minutes. The protein block was prepared as follows: PBS+1% bovine serum albumin (BSA); 0.5% casein; and 3% donkey serum.

Following the protein block, the primary antibodies AME-133 V, Human IgG1, or none were applied to the slides at a concentration of 10 μg/mL for 1 hour. Then, the slides were rinsed twice with PBS, and the biotinylated secondary antibody (donkey anti-human IgG) was applied to the slides for 30 minutes. Next, the slides were rinsed twice with PBS, reacted for 30 minutes with the ABC Elite reagent, and rinsed twice with PBS. Next, DAB was applied for 4 minutes as a substrate for the peroxidase reaction. All slides were rinsed with tap water, counterstained, dehydrated, and mounted. PBS+1% BSA served as the diluent for primary antibodies and ABC Elite reagent. (PBS+1% BSA)+ canine IgG (1:25 dilution) served as the diluent for the secondary antibody.

K9LO-133 Staining

The indirect immunoperoxidase procedure can be used to stain the canine lymphoma tissue with K9LO-133 to detect CD20. The requirement for labeling (e.g. biotin, peroxidase, or fluorescein) of 1K9LO-133 and preclusion of nonspecific reactivity between the secondary' labeled anti-canine IgG and IgG endogenous to the tissues examined can be eliminated according to the following process. The labeled secondary antibody was allowed to attach specifically to the unlabeled primary antibody (K9LO-133, DglgG, or none) by overnight incubation of the primary/secondary antibody mixtures prior to application to the tissue cryosections. The detection reagent or negative control antibody (at a concentration of 10 ^ig/niL) was mixed with biotinylated rabbit anti-dog IgG, Fc fragment-specific antibody (RbaDglgG) at a concentration of 15 μg/mL to achieve a primary: secondary antibody ratio of 1:1.5 on the day prior to staining.

Precomplexed antibodies were incubated overnight on a rocker mechanism in a refrigerator set to maintain 4° C., Prior to use of the antibody on the subsequent day, dog gamma globulins were added to each vial to achieve a final concentration of 3 mg/mL, and then incubated for at least 2 hours on the rocker mechanism in a refrigerator set to maintain 4° C. Slides were fixed in acetone for 10 minutes at room temperature at the time of sectioning. On the day of staining, the slides were rinsed twice with Tris-buffered saline, 0.15M NaCl, pH 7.6 TBS. Endogenous peroxidase was then quenched by incubation of the slides with an appropriate reagent such as Biocare PeroxAbolish reagent for 5 minutes at room temperature. Next, the slides were rinsed twice with TBS, incubated with the avidin solution for 15 minutes, rinsed once with TBS, incubated with the biotin solution for 15 minutes, and rinsed once with TBS, The slides were then treated with a protein block designed to reduce nonspecific binding for 20 minutes.

The protein block was prepared as follows: TBS+1% bovine serum albumin (BSA); 0.5% casein; and 3% normal rabbit serum. Following the protein block, the precomplexed primary and secondary antibodies were applied to the slides for two hours. Next, the slides were rinsed twice with TBS, treated with the ABC Elite reagent for 30 minutes, rinsed twice with TBS, and then treated with DAB for 4 minutes as a substrate for the peroxidase reaction. All slides were rinsed with tap water, counterstained, dehydrated, and mounted. TBS+1% B3SA served as the diluent for all antibodies and ABC reagent. Each staining run included a positive control (mononuclear leucocytes), and a negative control (smooth myocytes) of cryosections of canine spleen.

```
SEQ ID NO: 1; PRT; Artificial Sequence
EVQLVQSGAEVKKPGESLKISCKGSGRTFTSYNMHWVRQMPGKGLEWMGA
IYPLTGDTSYNQKSKLQVTISADKSISTAYLQWSSLKASDTAMYYCARST
YVGGDWQFDVWGKGTTVTVSSASTTAPSVFPLAPSCGSQSGSTVALACLV
SGYIPEPVTVSWNSGSLTSGVHTFPSVLOSSGLYSLSSMVTVPSSRWPSE
TFTCNVAHPATNTKVDKPVPKRENGRVPRPPDCPKCPAPELLGGPSVFIF
PPKPKDTLLIARTPEVTCVVVDLDPENPEVQISWFVDSKQVQTANTQPRE
EQSNGTYRVVSVLPIGHQDWLSGKQFKCKVNNKALPSPIEEIISKTPGQA
HQPNVYVLPPSRDEMSKNTVTLTCLVKDFFPPEIDVEWQSNGQQEPESKY
RMTPPQLDEDGSYFLYSKLSVDKSRWQRGDTFICAVMHEALHNHYTQISL
SHSPGK SEQ ID NO: 2; DNA; Artificial Sequence
GAGGTGCAGCTGGTGCAGTCTGGAGCAGAGGTGAAAAAGCCCGGGGAGTC
TCTGAAGATCTCCTGTAAGGGTTCTGGCCGTACATTTACCAGTTACAATA
TGCACTGGGTGCGCCAGATGCCCGGGAAAGGCCTGGAGTGGATGGGGGCT
ATTTATCCCTTGACGGGTGATACTTCCTACAATCAGAAGTCGAAACTCCA
GGTCACCATCTCAGCCGACAAGTCCATCAGCACCGCCTACCTGCAGTGGA
GCAGCCTGAAGGCCTCGGACACCGCCATGTATTACTGTGCGAGATCGACT
TACGTGGGCGGTGACTGGCAGTTCGATGTCTGGGGCAAGGGGACCACGGT
```

-continued
CACCGTCTCCTCAGCCTCCACCACGGCCCCCTCGGTTTTCCCGCTAGCGC
CCAGCTGTGGGTCCCAATCCGGCTCCACGGTGGCCCTGGCCTGCCTGGTG
TCAGGCTACATCCCCGAGCCTGTAACTGTGTCCTGGAATTCCGGCTCCTT
GACCAGCGGTGTGCACACCTTCCCGTCCGTCCTGCAGTCCTCAGGGCTCT
ACTCCCTCAGCAGCATGGTGACAGTGCCCTCCAGCAGGTGGCCCAGCGAG
ACCTTCACCTGCAATGTGGCCCACCCGGCCACCAACACTAAAGTAGACAA
GCCAGTGCCCAAAAGAGAAATGGAAGAGTTCCTCGCCCACCTGATTGTC
CCAAATGCCCAGCCCCTGAACTGCTGGGAGGGCCTTCGGTCTTCATCTTT
CCCCCAAAACCCAAGGACACCCTCTTGATTGCCCGAACACCTGAGGTCAC
ATGTGTGGTGGTGGATCTGGACCCAGAAAACCCTGAGGTGCAGATCAGCT
GGTTCGTGGATAGTAAGCAGGTGCAAACAGCCAACACGCAGCCTCGTGAG
GAGCAGTCCAATGGCACCTACCGTGTGGTCAGTGTCCTCCCCATTGGGCA
CCAGGACTGGCTTTCAGGGAAGCAGTTCAAGTGCAAAGTCAACAACAAAG
CCCTCCCATCCCCCATTGAGGAGATCATCTCCAAGACCCCACGGGCAGGC
CCATCAGCCTAATGTGTATGTCCTGCCGCCATCGCGGGATGAGATGAGCA
AGAATACGGTCACCCTGACCTGTCTGGTCAAAGACTTCTTCCCACCTGAG
ATTGATGTGGAGTGGCAGAGCAATGGACAGCAGGAGCCTGAGAGCAAGTA
CCGCATGACCCCGCCCCAGCTGGATGAAGATGGGTCCTACTTCCTATACA
GCAAGCTCTCCGTGGACAAGAGCCGCTGGCAGCGGGGAGACACCTTCATA
TGTGCGGTGATGCATGAAGCTCTACAACCACTACACACAGATATCCCT
CTCCCATTCTCCGGGTAAATGATGATAG SEQ ID NO: 3; PRT; Artificial Sequence
EVQLVQSGAEVKKPGESLKISCKGSGRTFTSYNMHWVRQMPGKGLEWMGA
IYPLTGDTSYNQKSKLQVTISADKSISTAYLQWSSLKASDTAMYYCARST
YVGGDWQFDVWGKGTTVTVSS SEQ ID NO: 4; PRT; Artificial Sequence
EVQLEVQSGAEVKKPGESLKISC SEQ ID NO: 5; PRT; Artificial Sequence
KGSGRTFTSYNMH SEQ ID NO: 6; PRT; Artificial Sequence
WVRQMPGKGLEWMG SEQ ID NO: 7; PRT; Artificial Sequence
AIYPLTGDTSYNQKSKL SEQ ID NO: 8; PRT; Artificial Sequence
QVTISADKSISTAYLQWSSLKASDTAMYYC SEQ ID NO: 9; PRT; Artificial Sequence
ARSTYVGGDWQFDV SEQ ID NO: 10; PRT; Artificial Sequence
EIVLTQSPGTLSLSPGERATLSCRASRSVPYIHWYQQKPGQAPRLLIYAT
SALASGIPDRFSGSGSGTDFTLTISRLEPEDFAVYYCQQWLSNPPTFGQG
TKLEIKRNDAQPAVYLFQPSPDQLHTGSASVVCLLNSFYPKDINVKWKVD
GVIQDTGIQESVTEQDKDSTYSLSSTLTMSSTEYLSHELYSCEITHKSLP
STLIKSFQRSECQRVD SEQ ID NO: 11; DNA; Artificial Sequence
GAAATTGTGTTGACGCAGTCTCCAGGCACCCTGTCTTTGTCTCCAGGGGA
AAGAGCCACCCTCTCCTGCAGGGCCAGCCGGAGTGTACCGTACATCCACT
GGTACCAGCAGAAACCTGGCCAGGCTCCCAGGCTCCTCATCTATGCCACA
TCCGCTCTGGCTTCTGGCATCCCAGACAGGTTCAGTGGCAGTGGGTCTGG
GACAGACTTCACTCTCACCATCAGCAGACTGGAGCCTGAAGATTTTGCAG
TGTATTACTGTCAGCAGTGGCTGAGTAACCCACCCACTTTTGGCCAGGGG
ACCAAGCTGGAGATCAAACGAATGATGCCCAGCCAGCCGTCTATTTGTT
CCAACCATCTCCAGACCAGTTACACACAGGAAGTGCCTCTGTTGTGTGCT
TGCTGAATAGCTTCTACCCCAAAGACATCAATGTCAAGTGGAAAGTGGAT
GGTGTCATCCAAGACACAGGCATCCAGGAAAGTGTCACAGAGCAGGACAA
GGACAGTACCTACAGCCTCAGCAGCACCCTGACGATGTCCAGTACTGAGT
ACCTAAGTCATGAGTTGTACTCCTGTGAGATCACTCACAAGAGCCTGCCC
TCCACCCTCATCAAGAGCTTCCAAAGGAGCGAGTGTCAGAGAGTGGAC SEQ ID NO: 12; PRT; Artificial Sequence
EIVLTQSPGTLSLSPGERATLSCRASRSVPYIHWYQQKPGQAPRLLIYAT
SALASGIPDRFSGSGSGTDFTLTISRLEPEDFAVYYCQQWLSNPPTFGQG
TKLEIK SEQ ID NO: 13; PRT; Artificial Sequence
EIVLTQSPGTLSLSPGERATLSC SEQ ID NO: 14; PRT; Artificial Sequence
RASRSVPYIH SEQ ID NO: 15; PRT; Artificial Sequence
WYQQKPGQAPRLLI SEQ ID NO: 16; PRT; Artificial Sequence
YATSALAS SEQ ID NO: 17; PRT; Artificial Sequence
GIPDRFSGSGSGTDFTLTISRLEPEDFAVYYC SEQ ID NO: 18; PRT; Artificial Sequence
QQWLSNPPT SEQ ID NO: 19; PRT; Artificial Sequence
FGQGTKLEIK

What is claimed is:

1. A method of detecting CD20 in a sample: said method comprising:
   a) contacting a sample with an antibody selective for canine CD20; wherein said antibody comprises:
   a light chain variable region (LCVR) whose amino acid sequence is that given in SEQ ID NO: 12, and a heavy chain variable region (HCVR) whose amino acid sequence is that given in SEQ ID NO: 3; or
   a light chain variable region (LCVR) comprising a first complementary determining region (LCDR1) whose amino acid sequence is that given in SEQ ID NO: 14, a second CDR (LCDR2) whose amino acid sequence is that given in SEQ ID NO: 16, a third CDR (LCDR3) whose amino acid sequence is that given in SEQ ID NO: 18, and a joining (J) region whose amino acid sequence is that given in SEQ ID NO: 19; and a heavy chain variable region (HCVR) comprising a first CDR (HCDR1) whose amino acid sequence is that given in SEQ ID NO: 5, a second CDR (HCDR2) whose amino acid sequence is that given in SEQ ID NO: 7, and a third CDR (HCDR3) whose amino acid sequence is that given in SEQ ID NO: 9; and wherein the antibody specifically binds to canine CD20; and
   b) washing the sample, and
   c) detecting the antibody selective for canine CD20.

2. The method according to claim 1, wherein the sample comprises canine lymphoma tissue.

3. The method according to claim 2, wherein the sample comprises a tissue cryosection.

4. The method according to claim 1, wherein the method further comprises contacting the sample with a second antibody; wherein the second antibody is selective for the antibody selective for canine CD20.

5. The method according to claim 1, wherein the antibody selective for canine CD20 is labeled.

6. A kit, comprising a pharmaceutical composition, comprising an antibody which specifically binds to canine CD20, with one or more pharmaceutically acceptable carriers, diluents, or excipients and a chemotherapeutic agent;
   wherein the antibody which specifically binds to canine CD20 comprises a light chain variable region (LCVR)

comprising a LCDR1 of SEQ ID NO: 14, a LCDR2 of SEQ ID NO: 16, a LCDR3 of SEQ ID NO: 18, and a J region of SEQ ID NO: 19; and a heavy chain variable region (HCVR) comprising a HCDR1 of SEQ ID NO: 5, a HCDR2 of SEQ ID NO: 7, and a HCDR3 of SEQ ID NO: 9.

7. A kit, comprising a pharmaceutical composition, comprising an antibody which specifically binds to canine CD20, with one or more pharmaceutically acceptable carriers, diluents, or excipients and a chemotherapeutic agent;
wherein the antibody which specifically binds to canine CD20 comprises a light chain variable region (LCVR) whose amino acid sequence is that given in SEQ ID NO: 12, and a heavy chain variable region (HCVR) whose amino acid sequence is that given in SEQ ID NO: 3.

* * * * *

```
                         SEQUENCE LISTING

Sequence total quantity: 19
SEQ ID NO: 1            moltype = AA   length = 456
FEATURE                 Location/Qualifiers
REGION                  1..456
                        note = Chimeric human/dog anti-CD20 antibody
source                  1..456
                        mol_type = protein
                        organism = synthetic construct
SEQUENCE: 1
EVQLVQSGAE VKKPGESLKI SCKGSGRTFT SYNMHWVRQM PGKGLEWMGA IYPLTGDTSY  60
NQKSKLQVTI SADKSISTAY LQWSSLKASD TAMYYCARST YVGGDWQFDV WGKGTTVTVS 120
SASTTAPSVF PLAPSCGSQS GSTVALACLV SGYIPEPVTV SWNSGSLTSG VHTFPSVLQS 180
SGLYSLSSMV TVPSSRWPSE TFTCNVAHPA TNTKVDKPVP KRENGRVPRP PDCPKCPAPE 240
LLGGPSVFIF PPKPKDTLLI ARTPEVTCVV VDLDPENPEV QISWFVDSKQ VQTANTQPRE 300
EQSNGTYRVV SVLPIGHQDW LSGKQFKCKV NNKALPSPIE EIISKTPGQA HQPNVYVLPP 360
SRDEMSKNTV TLTCLVKDFF PPEIDVEWQS NGQQEPESKY RMTPPQLDED GSYFLYSKLS 420
VDKSRWQRGD TFICAVMHEA LHNHYTQISL SHSPGK                           456

SEQ ID NO: 2            moltype = DNA  length = 1377
FEATURE                 Location/Qualifiers
misc_feature            1..1377
                        note = Chimeric human/dog anti--CD20 antibody
source                  1..1377
                        mol_type = other DNA
                        organism = synthetic construct
SEQUENCE: 2
```

-continued

```
gaggtgcagc tggtgcagtc tggagcagag gtgaaaaagc ccggggagtc tctgaagatc   60
tcctgtaagg gttctggccg tacatttacc agttacaata tgcactgggt gcgccagatg  120
cccgggaaag gcctggagtg gatgggggct atttatccct tgacgggtga tacttcctac  180
aatcagaagt cgaaactcca ggtcaccatc tcagccgaca gtccatcagc accgcctac   240
ctgcagtgga gcagcctgaa ggcctcggac accgccatgt attactgtgc agatcgact   300
tacgtgggcg gtgactggca gttcgatgtc tggggcaagg ggaccacggt caccgtctcc  360
tcagcctcca ccacggcccc ctcggttttc ccgctagcgc ccagctgtgg gtcccaatcc  420
ggctccacgg tggccctggc ctgcctggtg tcaggctaca tccccgagcc tgtaactgtg  480
tcctggaatt ccggctcctt gaccagcggt gtgcacacct tcccgtccgt cctgcagtcc  540
tcagggctct actccctcag cagcatggtg acagtgccct ccagcaggtg gcccagcgag  600
accttcacct gcaatgtggc caccccggcc accaacacta agtagacaa gccagtgccc   660
aaaagagaaa atggaagagt tcctcgccca cctgattgtc ccaaatgccc agcccctgaa  720
ctgctgggag ggccttcggt cttcatcttt cccccaaaac ccaaggacac cctcttgatt  780
gcccgaacac ctgaggtcac atgtgtggtg gtggatctgg acccagaaaa ccctgaggtg  840
cagatcagct ggttcgtgga tagtaagcag gtgcaaacag ccaacacgca gcctcgtgag  900
gagcagtcca atggcaccta ccgtgtgtgt agtgtcctcc ccattgggca ccaggactgg  960
ctttcaggga agcagttcaa gtgcaaagtc aacaacaaag ccctcccatc cccccattgag 1020
gagatcatct ccaagacccc agggcaggcc catcagccta atgtgtatgt cctgccgcca 1080
tcgcgggatg agatgagcaa gaatacggtc accctgacct gtctggtcaa agacttcttc  1140
ccacctgaga ttgatgtgga gtggcagagc aatggacagc aggagcctga gagcaagtac 1200
cgcatgaccc cgccccagct ggatgaagat gggtcctact tcctatacag caagctctcc 1260
gtggacaaga gccgctggca gcggggagac accttcatat gtgcggtgat gcatgaagct 1320
ctacaaacc actacacaca gatatccctc tcccattctc cgggtaaatg atgatag     1377
```

```
SEQ ID NO: 3              moltype = AA  length = 121
FEATURE                   Location/Qualifiers
REGION                    1..121
                          note = Chimeric human/dog anti-CD20 antibody
source                    1..121
                          mol_type = protein
                          organism = synthetic construct
SEQUENCE: 3
EVQLVQSGAE VKKPGESLKI SCKGSGRTFT SYNMHWVRQM PGKGLEWMGA IYPLTGDTSY   60
NQKSKLQVTI SADKSISTAY LQWSSLKASD TAMYYCARST YVGGDWQFDV WGKGTTVTVS  120
S                                                                 121

SEQ ID NO: 4              moltype = AA  length = 22
FEATURE                   Location/Qualifiers
REGION                    1..22
                          note = Chimeric human/dog anti-CD20 antibody
source                    1..22
                          mol_type = protein
                          organism = synthetic construct
SEQUENCE: 4
EVQLVQSGAE VKKPGESLKI SC                                           22

SEQ ID NO: 5              moltype = AA  length = 13
FEATURE                   Location/Qualifiers
REGION                    1..13
                          note = Chimeric human/dog anti-CD20 antibody
source                    1..13
                          mol_type = protein
                          organism = synthetic construct
SEQUENCE: 5
KGSGRTFTSY NMH                                                     13

SEQ ID NO: 6              moltype = AA  length = 14
FEATURE                   Location/Qualifiers
REGION                    1..14
                          note = Chimeric human/dog anti-CD20 antibody
source                    1..14
                          mol_type = protein
                          organism = synthetic construct
SEQUENCE: 6
WVRQMPGKGL EWMG                                                    14

SEQ ID NO: 7              moltype = AA  length = 17
FEATURE                   Location/Qualifiers
REGION                    1..17
                          note = Chimeric human/dog anti-CD20 antibody
source                    1..17
                          mol_type = protein
                          organism = synthetic construct
SEQUENCE: 7
AIYPLTGDTS YNQKSKL                                                 17

SEQ ID NO: 8              moltype = AA  length = 30
FEATURE                   Location/Qualifiers
REGION                    1..30
```

-continued

```
                        note = Chimeric human/dog anti-CD20 antibody
source                  1..30
                        mol_type = protein
                        organism = synthetic construct
SEQUENCE: 8
QVTISADKSI STAYLQWSSL KASDTAMYYC                                      30

SEQ ID NO: 9            moltype = AA  length = 14
FEATURE                 Location/Qualifiers
REGION                  1..14
                        note = Chimeric human/dog anti-CD20 antibody
source                  1..14
                        mol_type = protein
                        organism = synthetic construct
SEQUENCE: 9
ARSTYVGGDW QFDV                                                       14

SEQ ID NO: 10           moltype = AA  length = 216
FEATURE                 Location/Qualifiers
REGION                  1..216
                        note = Chimeric human/dog anti-CD20 antibody
source                  1..216
                        mol_type = protein
                        organism = synthetic construct
SEQUENCE: 10
EIVLTQSPGT LSLSPGERAT LSCRASRSVP YIHWYQQKPG QAPRLLIYAT SALASGIPDR      60
FSGSGSGTDF TLTISRLEPE DFAVYYCQQW LSNPPTFGQG TKLEIKRNDA QPAVYLFQPS     120
PDQLHTGSAS VVCLLNSFYP KDINVKWKVD GVIQDTGIQE SVTEQDKDST YSLSSTLTMS     180
STEYLSHELY SCEITHKSLP STLIKSFQRS ECQRVD                              216

SEQ ID NO: 11           moltype = DNA  length = 648
FEATURE                 Location/Qualifiers
misc_feature            1..648
                        note = Chimeric human/dog anti-CD20 antibody
source                  1..648
                        mol_type = other DNA
                        organism = synthetic construct
SEQUENCE: 11
gaaattgtgt tgacgcagtc tccaggcacc ctgtctttgt ctccagggga aagagccacc     60
ctctcctgca gggccagccg gagtgtaccg tacatccact ggtaccagca gaaacctggc    120
caggctccca ggtcctcat ctatgccaca tccgctctgg cttctggcat cccagacagg    180
ttcagtggca gtgggtctgg gacagacttc actctcacca tcagcagact ggagcctgaa    240
gattttgcag tgtattactg tcagcagtgg ctgagtaacc cacccacttt tggccagggg    300
accaagctgg agatcaaacg aaatgatgcc cagccagccg tctatttgtt ccaaccatct    360
ccagaccagt tacacacagg aagtgcctct gtttgtgtgct tgctgaatag cttctacccc    420
aaagacatca atgtcaagtg gaaagtggat ggtgtcatcc aagacacagg catccaggaa    480
agtgtcacag agcaggacaa ggacagtacc tacagcctca gcagcaccct gacgatgtcc    540
agtactgagt acctaagtca tgagttgtac tcctgtgaga tcactcacaa gagcctgccc    600
tccacccta tcaagagctt ccaaaggagc gagtgtcaga gagtggac                648

SEQ ID NO: 12           moltype = AA  length = 106
FEATURE                 Location/Qualifiers
REGION                  1..106
                        note = Chimeric human/dog anti-CD20 antibody
source                  1..106
                        mol_type = protein
                        organism = synthetic construct
SEQUENCE: 12
EIVLTQSPGT LSLSPGERAT LSCRASRSVP YIHWYQQKPG QAPRLLIYAT SALASGIPDR      60
FSGSGSGTDF TLTISRLEPE DFAVYYCQQW LSNPPTFGQG TKLEIK                   106

SEQ ID NO: 13           moltype = AA  length = 23
FEATURE                 Location/Qualifiers
REGION                  1..23
                        note = Chimeric human/dog anti-CD20 antibody
source                  1..23
                        mol_type = protein
                        organism = synthetic construct
SEQUENCE: 13
EIVLTQSPGT LSLSPGERAT LSC                                             23

SEQ ID NO: 14           moltype = AA  length = 10
FEATURE                 Location/Qualifiers
REGION                  1..10
                        note = Chimeric human/dog anti-CD20 antibody
source                  1..10
                        mol_type = protein
                        organism = synthetic construct
SEQUENCE: 14
```

```
RASRSVPYIH                                                                      10

SEQ ID NO: 15           moltype = AA  length = 14
FEATURE                 Location/Qualifiers
REGION                  1..14
                        note = Chimeric human/dog anti-CD20 antibody
source                  1..14
                        mol_type = protein
                        organism = synthetic construct
SEQUENCE: 15
WYQQKPGQAP RLLI                                                                 14

SEQ ID NO: 16           moltype = AA  length = 8
FEATURE                 Location/Qualifiers
REGION                  1..8
                        note = Chimeric human/dog anti-CD20 antibody
source                  1..8
                        mol_type = protein
                        organism = synthetic construct
SEQUENCE: 16
YATSALAS                                                                        8

SEQ ID NO: 17           moltype = AA  length = 32
FEATURE                 Location/Qualifiers
REGION                  1..32
                        note = Chimeric human/dog anti-CD20 antibody
source                  1..32
                        mol_type = protein
                        organism = synthetic construct
SEQUENCE: 17
GIPDRFSGSG SGTDFTLTIS RLEPEDFAVY YC                                              32

SEQ ID NO: 18           moltype = AA  length = 9
FEATURE                 Location/Qualifiers
REGION                  1..9
                        note = Chimeric human/dog anti-CD20 antibody
source                  1..9
                        mol_type = protein
                        organism = synthetic construct
SEQUENCE: 18
QQWLSNPPT                                                                       9

SEQ ID NO: 19           moltype = AA  length = 10
FEATURE                 Location/Qualifiers
REGION                  1..10
                        note = Chimeric human/dog anti-CD20 antibody
source                  1..10
                        mol_type = protein
                        organism = synthetic construct
SEQUENCE: 19
FGQGTKLEIK                                                                      10
```